US007431925B2

(12) United States Patent
Rajagopalan et al.

(10) Patent No.: US 7,431,925 B2
(45) Date of Patent: Oct. 7, 2008

(54) INTERNAL IMAGE ANTIBODIES FOR OPTICAL IMAGING AND THERAPY

(75) Inventors: Raghavan Rajagopalan, Beechwood, OH (US); Joseph E. Bugaj, St. Charles, MI (US); Samuel I. Achilefu, St. Louis, MI (US); Richard B. Dorshow, St. Louis, MI (US)

(73) Assignee: Mallinckrodt, Inc., St. Louis, MO (US)

( * ) Notice: Subject to any disclaimer, the term of this patent is extended or adjusted under 35 U.S.C. 154(b) by 406 days.

(21) Appl. No.: 10/761,634

(22) Filed: Jan. 21, 2004

(65) Prior Publication Data

US 2004/0151667 A1 Aug. 5, 2004

Related U.S. Application Data

(62) Division of application No. 09/919,243, filed on Jul. 31, 2001, now abandoned.

(51) Int. Cl.
*A61K 39/395* (2006.01)
*C07K 16/42* (2006.01)
(52) U.S. Cl. .................. 424/131.1; 424/9.6; 424/178.1; 424/179.1; 530/387.2; 530/391.3; 530/391.5
(58) Field of Classification Search .................. 424/9.6, 424/9.61, 131.1; 436/548
See application file for complete search history.

(56) References Cited

U.S. PATENT DOCUMENTS

| | | | | |
|---|---|---|---|---|
| 3,996,345 | A | 12/1976 | Ullman et al. | 424/12 |
| 4,536,479 | A | 8/1985 | Vander-Mallie | 436/537 |
| 4,659,839 | A | 4/1987 | Nicolotti et al. | 548/546 |
| 4,683,295 | A * | 7/1987 | Carson | 424/131.1 |
| 4,732,974 | A | 3/1988 | Nicolotti et al. | 530/390 |
| 4,818,684 | A | 4/1989 | Edelman et al. | 435/7 |
| 4,837,003 | A | 6/1989 | Nicolotti | 424/1.1 |
| 4,965,392 | A | 10/1990 | Fritzberg et al. | 558/254 |
| 5,518,888 | A | 5/1996 | Waldman | 435/7.23 |
| 5,571,696 | A * | 11/1996 | Evans et al. | 435/69.1 |
| 5,667,764 | A | 9/1997 | Kopia et al. | 424/1.45 |
| 5,716,595 | A * | 2/1998 | Goldenberg | 424/1.49 |
| 6,083,485 | A | 7/2000 | Licha et al. | 424/9.6 |
| 6,258,340 | B1 | 7/2001 | Licha et al. | 424/9.6 |
| 6,485,704 | B1 | 11/2002 | Rajagopalan et al. | 424/9.1 |
| 2004/0151667 | A1 * | 8/2004 | Rajagopalan et al. | 424/9.6 |

FOREIGN PATENT DOCUMENTS

| | | |
|---|---|---|
| EP | 0386275 A2 | 9/1990 |
| EP | 0 476 408 | 3/1992 |
| EP | 0284071 B1 | 6/1994 |
| WO | WO 93/00934 | 1/1993 |
| WO | WO 98/08859 | 3/1998 |
| WO | WO 98/47538 | 10/1998 |
| WO | WO 00/41727 | 7/2000 |
| WO | WO 02/100326 | 12/2002 |

OTHER PUBLICATIONS

Cruse et al, Illustrated Dictionary of Immunology, CRC Press, Inc. 1995, p. 172.*
Roitt, Essential Immunology, Fifth Edition, Blackwell Scientific Publications, 1984, p. 106.*
PCT, *Supplementary Partial European Search Report*, Application No. 02756510.00-2107, PCT/US0222755, mailed Sep. 19, 2005.
ISA/US, *International Search Report*, PCT/US02/22755, Dated Sep. 8, 2004 (4 pages).
Sternberger, *Immunocytochemistry*, Prentice-Hall, Inc., 1974, pp. 22-23.
Kohler and Milstein, *Continuous cultures of fused cells secreting antibody of predefined specificity*, Nature 256, 1975, pp. 495-497.
Licha et al., *Synthesis and characterization of cyanine dyes as contrast agents for near-infrared imaging*, The Society of Photo-Optical Instrumentation Engineers, vol. 2927, 1996, pp. 192-198.
Li et al., *Tumor Localization Using Fluorescence of Indocyanine Green (ICG) In Rat Models*, The Society of Photo-Optical Instrumentation Engineers, vol. 2389, 1995, pp. 789-797.
Riefke et al., *In vivo characterization of cyanine dyes as contrast agents for near-infrared imaging*, The Society of Photo-Optical Instrumentation Engineers, vol. 2927, 1996, pp. 199-208.
Pak et al., *Technitium-99M Labeling Of A Tumor Specific Mouse/ Human Chimeric Antibody Having a Human 3 Constant Region*, The Journal Of Nuclear Medicine, vol. 30, No. 872, p. 934.
Ballou et al., *Tumor labeling in vivo using cyanine-conjugated monoclonal antibodies*, Cancer Immunology and Immunotherapy, vol. 41, 1995, pp. 257-263.
Achilefu et al., *Novel Receptor-Targeted Fluorescent Contrast Agents for In Vivo Tumor Imaging*, Investigative Radiology, vol. 35, No. 8, 2000, pp. 479-485.
Licha et al., *New Contrast Agents for Optical Imaging: Acid-Cleavable Conjugates of Cyanine Dyes with Biomolecules*, The Society of Photo-Optical Instrumentation Engineers, vol. 3600, 1999, pp. 29-35.
Cayanis et al., *Generation of an Auto-anti-idiotypic Antibody That Binds to Glucocorticoid Receptor*, The Journal of Biological Chemistry, vol. 261, No. 11, 1986, pp. 5094-5103.
Erlanger et al., *The Auto-Anti-Idiotypic Route To Anti-Receptor Antibodies*, in Idiotypes, Academic Press, 1986, pp. 157-178.
Jori, *Novel Therapeutic Modalities Based on Photosensitized Processes*, EPA Newsletter, No. 60, Jul. 1997, pp. 12-18.
Jeme, *Idiotypic Networks and Other Preconceived Ideas*, Immunological Reviews, vol. 79, 1984, pp. 5-24.

(Continued)

*Primary Examiner*—David A Saunders
(74) *Attorney, Agent, or Firm*—Thompson Hine LLP (57) ABSTRACT

Methods using internal image antibodies for photodiagnosis and/or phototherapy. The internal image antibodies are conjugated with a photoactive molecule such as a dye or photosensitizer, to target specific regions, such as biological receptors. The photoactive molecules are then activated for diagnosis or therapy. Advantageously, the internal image antibody is specific for a biological receptor, but does not require isolation of the receptor to prepare the antibody, and provides the desired specificity and selectivity for targeted diagnosis or therapy.

12 Claims, 2 Drawing Sheets

OTHER PUBLICATIONS

Parham et al., *Monoclonal Antibodies: Purification, Fragmentation and Application to Structural and Functional Studies of Clas I MHC Antigens*, Journal of Immunological Methods, vol. 53, 1982, pp. 133-173.

Martin and Cook, *Table V-Buffer Mixtures, in Remington's Practice of Pharmacy*, 1956, p. 170.

Pandurangi et al., *Chemistry of Bifunctional Photoprobes. 3. Correlation between the Efficiency of CH Insertion by Photolabile Chelating Agents and Lifetimes of Singlet Nitrenes by Flash Photolysis: First Example of Photochemical Attachment of 99mTc-Complex with Human Se*, Journal of Organic Chemistry, vol. 63, 1998, pp. 9019-9030.

Mariani et al., *A New Enzymatic Method To Obtain High-Yield F(ab)2 Suitable For Clinical Use From Mouse IgG1*, Molecular Immunology, vol. 28, No. ½, 1991, pp. 69-77.

Erlanger, *Auto-Anti-Idiotypy, Autoimmunity and Some Thoughts on the Structure of Internal Images*, International Review of Immunology, vol. 5, 1989, pp. 131-137.

Leu et al., *Idiotypic mimicry and the assembly of a supramolecular structure: An anti-idiotypic antibody that mimics taxol in its tubulin-microtubule interactions*, Proceedings of the National Academy of Science, vol. 91, 1994, pp. 10690-10694.

Hebden and Delpy, *Diagnostic imaging with light*, The British Journal of Radiology, vol. 70, 1997, S206-S214.

Freiherr, *The Light Stuff: Optical Imaging in Medical Diagnosis*, R&D Horizons, Medical Device & Diagnostic Industry, 1998, pp. 1-7.

Stables and Ash, *Photodynamic therapy*, Cancer Treatment Reviews, vol. 21, 1995, pp. 311-323.

Korbelik, *Photosensitizers in photodynamic therapy*, Periodicum Biologorum, vol. 93, No. 4, 1991, pp. 563-574.

Desvergne and Czarnik, *Chemossensors of Ion and Molecule Recognition*, Series C: Mathematical and Physical Sciences, vol. 492, 1997, table of contents.

\* cited by examiner

INTERNAL IMAGE ANTIBODIES FOR OPTICAL IMAGING AND THERAPY

RELATED APPLICATION

This application is a Divisional of and claims priority to U.S. patent application Ser. No. 09/919,243 filed Jul. 31, 2001, now abandoned and expressly incorporated by reference herein in its entirety.

FIELD OF THE INVENTION

The invention relates generally to diagnosis and therapy using photoactive compounds. More particularly, the invention relates to bioconjugates comprising internal image antibodies or their fragments attached to photoactive molecules.

BACKGROUND OF THE INVENTION

The use of visible, near-infrared (NIR), and low-energy ultraviolet light in clinical practice is growing rapidly. Compounds absorbing or emitting in the visible, NIR, or long wavelength (UV-A, >350 nm) region of the electromagnetic spectrum are potentially useful for diagnostic techniques such as tomographic or planar imaging, endoscopic examination, optoacoustic imaging and sonofluorescene imaging.

Notwithstanding the importance of photodiagnostic applications, a major advantage of biomedical optics lies in its therapeutic potential. Phototherapy has been demonstrated to be a safe and effective procedure for the treatment of various surface lesions, both external and internal. Its efficacy is comparable to radiotherapy, but without the harmful radiotoxicity to critical non-target organs.

The use of fluorescent dyes and covalent dye conjugates for the detection of various species in body fluids is well known in the field of in-vitro immunodiagnostics. Fluorescent dyes have also been used as chemosensors and in fluorescence microscopy. Dyes and dye-immunoconjugates have been widely used in immunohistology, and in immunochemical detection of various small and large biomolecules in body fluids using enzyme-linked immunosorbent assay (ELISA) procedures. More recently, indocyanine green, a highly fluorescent polyene dye, has been used for monitoring cardiac output, assessing hepatic function, and tomographic imaging of tumors.

Specific targeting of fluorescent dyes to a particular site, such as a tumor, has advantages over non-specific localization of these dyes in various tissues. A known method of targeting is by attaching the dye or other effector molecule to an antibody that binds at a target site. Antibodies can tolerate the attachment of a reasonable number of haptens, such as up to about five haptens, on their surfaces while still substantially retaining their binding properties. In contrast, conjugation of haptens to molecules that are similar in size, such as drugs or hormones, most often but not always, obviate the binding properties of the effector molecule to the receptor. This is due to the fact that the large size of antibodies permits the attachment of haptens away from the combining site of the antibodies.

We have demonstrated that indocyanine green dye covalently attached to octreotate retains the somatostatin receptor binding properties, as reported in Achilefu et al., *Investigative Radiology*, 2000, vol. 35, p. 479, which is expressly incorporated by reference herein in its entirety. This observation, however, is not general and it is not possible at this time to predict a priori the binding properties of small molecule bioconjugates with a high degree of confidence. In contrast, the binding properties of antibody conjugates are generally predictable.

To target a receptor using antibodies, however, anti-receptor antibodies are required. Conventional methods of producing anti-receptor monoclonal antibodies require the isolation of pure receptors. This is often not possible for various reasons, including the lack of stability of many biological receptors. Thus, most receptor targeting with anti-receptor antibodies have been elusive.

The idiotypic network theory of Jerne (*Immunological Reviews*, 1984, 79, 5-24) proposes that the variable regions of antibodies (i.e. idiotypes) act as immunogens to give rise to a secondary set of antibodies, called anti-idiotypes. An anti-idiotypic antibody is an antibody raised against a first antibody.

The binding site of an antibody is the particular region of the antibody molecule which specifically binds to the recognized epitope. In particular, if antibodies are developed against a ligand that binds to a certain receptor within the body, then a subpopulation of the resulting anti-idiotypic population, which is referred to as 'internal images', may contain antibodies that will likewise bind to the same receptor, due to the sharing of a common epitope between the ligand and the internal image. Essentially, the anti-idiotypic antibody mimics the original ligand or drug that is specific to the particular biological receptor.

Application of the principles proposed by Jerne has led to the isolation of a number of internal image antibodies directed at various biological receptors, without ever having to isolate and purify the natural receptor. Examples of these receptors include receptors for thyroid stimulating hormone (TSH), glucocorticoid, and adenosine. Lue et al. (*Proceedings of the National Academy of Sciences*, 1994, 91, 10690-10694) have used this approach to study the mechanism of an anti-cancer compound, taxol. Thus, the use of internal image antibodies with photoactive molecules for photodiagnostic and phototherapeutic purposes is desirable.

SUMMARY OF THE INVENTION

The composition and use of internal image antibody conjugates to achieve specificity for photodiagnostic and phototherapeutic applications, without the need to isolate a particular receptor, are disclosed. The invention discloses novel bioconjugates of internal image anti-idiotypic antibodies, or antibody fragments which contain the desired epitope for binding (hereinafter referred to as antibody fragment), that are attached to photoactive molecules (PM) for photodiagnostic or phototherapeutic purposes. These are generally represented by the following structure:

where Ab is a whole internal image antibody or antibody fragment directed to a particular biological receptor and PM is a photoactive molecule such as dyes, photosensitizers or precursors for producing reactive intermediates. The internal image antibody is directed to a biological receptor, for example, receptors for steroids, cardiac glycosides, somatostatin, bombesin, cholecystokinen (CCK), neurotensin, or heat stable toxin. In some embodiments, a linker may link Ab and PM, represented as Ab-L-PM. The linker may be —HNCONH—, —HNCSNH—, —HNCO—, —CONH—, —S(CH$_2$)$_m$CONH—, or —S—(N-succinimido)-(CH$_2$)$_n$CONH—, with m and n varying from 1 to 10.

In one embodiment, the invention discloses novel bioconjugates of internal image antibodies or antibody fragments attached to a photoactive dye for photodiagnostic purposes. In this embodiment, PM is a dye and the conjugate has the general formula:

Ab-L-Dye where Ab is a whole or fragmented internal image antibody directed at a particular biological receptor and L is an optional linker. The dye may be a chromophore or a fluorophore useful for photodiagnostic purposes and may be derived from cyanines, indocyanines, phthalocyanines, rhodamines, phenoxazines, phenothiazines, phenoselenazines, fluoresceins, porphyrins, benzoporphyrins, squaraines, corrins, croconiums, azo compounds, methine dyes, and/or indolenium dyes.

In another embodiment, the invention discloses novel bioconjugates of internal image antibodies or antibody fragments attached to one or more photoactive molecules for phototherapeutic purposes. In this embodiment, PM is a photosensitizer (PS), which either by itself or associated with a precursor (Q), produces reactive intermediates. In this embodiment, the conjugate has the general formula:

Ab-L-PS-Q where Ab is as previously described; L is optional as previously described; PS is a photosensitizing aromatic or a heteroaromatic radical derived from benzenes, polyfluorobenzenes, naphthalenes, naphthoquinones, anthracenes, anthraquinones, phenanthrenes, tetracenes, naphthacenediones, pyridines, quinolines, isoquinolines, indoles, isoindoles, pyrroles, imidiazoles, pyrazoles, pyrazines, purines, benzimidazoles, benzofurans, dibenzofurans, carbazoles, acridines, acridones, phenanthridines, thiophenes, benzothiophenes, dibenzothiophenes, xanthenes, xanthones, flavones, coumarins, and anthracylines; and Q is either a precursor for producing reactive intermediates such as free radicals, nitrenes, carbenes, and the like, or may be an azide ($-N_3$), a cyclic azo compound ($-N=N-$), or a sulfenate ($-O-S-$).

The invention also discloses a method for performing a diagnostic procedure using internal image antibody bioconjugates. In the method, a ligand is selected that binds to a biological receptor, such as the receptor for steroids, cardiac glycosides, somatostatin, bombesin, cholecystokinen, neurotensin, and heat stable toxin. The receptor-binding ligand may be one or more drugs, hormones, peptides, carbohydrates, nucleosides, peptidomimetics, glycomimetics, or biosynthetic intermediates. The ligand used as the first generation antigen may be the complete ligand, or may be a certain region of the ligand such a fragment that binds the receptor with high affinity, etc. The receptor-binding ligand is prepared as a first generation antigen, optionally conjugating the receptor-binding ligand to an immunogenic carrier. The immunogenic carrier may be, for example, bovine serum albumin, rabbit serum albumin, or human serum albumin.

First generation monoclonal antibodies are generated against the first generation antigen, and the specific monoclonal antibodies directed to the desired receptor-binding ligands are isolated. Monoclonal anti-idiotypic antibodies against the first generation antibodies are then generated, and internal image anti-receptor antibodies from the population of anti-idiotypic antibodies are isolated. The internal image anti-receptor antibodies are then conjugated to a dye by conventional methods known to one skilled in the art.

In use, an effective amount of the internal image antibody conjugate is administered to a patient, and the conjugate is allowed to accumulate at the target site. The target site is then exposed to light having a wavelength in the range of 300 to 1200 nm, and having sufficient power and fluency to image the target tissue using, for example, absorbance, fluorescence, or scattering methods. The imaging can be obtained by a CCD camera or use optical tomographic equipment. All of these procedures are known to one skilled in the art.

The invention also discloses a method of performing a phototherapeutic procedure using internal image antibody bioconjugates. The internal image antibody and ligand are as previously described for use in a photodiagnostic method. Rather than a dye, however, a photosensitizer (PS) is conjugated to the internal image antibody and linker. The PS may be benzenes, polyfluorobenzenes, naphthalenes, naphthoquinones, anthracenes, anthraquinones, phenanthrenes, tetracenes, naphthacenediones, pyridines, quinolines, isoquinolines, indoles, isoindoles, pyrroles, imidiazoles, pyrazoles, pyrazines, purines, benzimidazoles, benzofurans, dibenzofurans, carbazoles, acridines, acridones, phenanthridines, thiophenes, benzothiophenes, dibenzothiophenes, xanthenes, xanthones, flavones, coumarins, and/or anthacylines. The PS may also be associated with a precursor (Q) which may be an azide ($-N_3$), a cyclo azo compound ($-N=N-$), or a sulfenate ($-O-S-$).

In use, an effective amount of the internal image antibody conjugate is administered to a patient, and the conjugate is allowed to accumulate at the target site. The target site is exposed to light having a wavelength in the range of 300 to 1200 nm with sufficient power and fluency to treat the impaired tissue, for example, by inducing necrosis or apoptosis.

The invention will be further appreciated in light of the following figures, detailed description, and examples.

DETAILED DESCRIPTION

The invention is directed to a diagnostic and/or therapeutic composition of an internal image antibody for a biological receptor (anti-receptor internal image antibody) that is conjugated to a photoactive molecule or molecules. This composition has the general formula:

Ab-PM where Ab is a whole or fragmented internal image antibody directed at a particular biological receptor and PM is a photoactive molecule or molecules such as a dye or a photosensitizer which either by itself or with an attached precursor produces reactive intermediates. A linker L may optionally be used to link Ab and PM, represented as Ab-L-PM.

For a diagnostic composition, the conjugate consists of an internal image antibody and a dye. For a therapeutic composition, the conjugate consists of an internal image antibody and a photosensitizer for producing reactive intermediates. The internal-image antibody may be a whole antibody, or may be antibody fragments that contain the desired epitope for binding which have been cleaved enzymatically or chemically to produce Fab, Fab', (Fab')$_2$, or other smaller fragments that retain antigen binding properties. The methods of cleaving antibodies to produce such fragments, and the uses of these fragments, are known to one of skill in the art. Method for preparing antibody fragments are known to one skilled in the art, for example, by enzymatic digestion with papain or pepsin of the whole antibody, as described by Parham et al. (*J. Immunol Methods*, 1982, 53, 133-173) and Mariani et al. (*Molecular Immunology*, 1991, 1991, 69-77), the relevant sections of each being expressly incorporated by reference herein.

The invention is also directed to a method for performing a medical procedure by administering an effective amount of a composition of the anti-receptor internal image antibody conjugate. Photodiagnostic and/or phototherapeutic agents are targeted to the desired site using receptor-specific internal image antibodies to receptors that are expressed at these sites. The method may be used in various biomedical applications, such as in the diagnosis and/or therapy of some types of coronary disorders, certain types of tumors, certain types of lesions, etc. These include, but are not limited to, diagnosis and/or therapy of regions that are necrotic, ischemic, thrombic, inflammatory, contain impaired vasculature, in which apoptosis is desirable, etc.

The use of internal image antibodies as carriers for targeted photodiagnostic and phototherapeutic applications is desirable, since it provides the benefit of high specificity without the problems associated with small molecule bioconjugates. The use of internal images in diagnostic and therapeutic medicine was first proposed by us (Rajagopalan, Tissue specific imaging agents using internal image anti-idiotypic antibodies, WO 93/00934). The inventive approach disclosed herein of utilizing internal image antibodies for targeting specific receptors has several advantages. Purified receptors need not be used to develop the anti-receptor antibodies; this is advantageous since it is often difficult and sometimes impossible to isolate pure, stable receptors for immunization. The receptor binding affinity of the original ligand and the corresponding internal image antibody is very similar. The attachment of an effector molecule, such as a photoactive agent or a photosensitizer, to the large antibody molecule does not significantly perturb its receptor binding capability.

Photosensitizers operate via two distinct pathways, termed Types 1 and 2. Type 1 mechanisms are shown in the following scheme:

Type 1 mechanism involves direct energy or electron transfer from the photosensitizer to the cellular components thereby causing cell death. Type 2 process involves two distinct steps as shown in the following scheme:

In the first step, singlet oxygen is generated by energy transfer from the triplet excited state of the photosensitizer to the oxygen molecules surrounding the tissues. In the second step, collision of a singlet oxygen with the tissues promotes tissue damage. In both Type 1 and Type 2 mechanisms, the photoreaction proceeds via the lowest triplet state of the sensitizer. Hence, a relatively long triplet lifetime is required for effective phototherapy, whereas a short triplet lifetime is necessary for photodiagnostics in order to avoid photo damage. The inventive method can be used in photodiagnostic or phototherapeutic applications operating by either the Type 1 or Type 2 mechanism, as described by Jori (*EPA Newsletter,* 1997, No. 60, 12-18), which is expressly incorporated by reference herein in its entirety.

Anti-idiotypic antibodies are made by developing antibodies against a first antibody that binds specifically to a certain ligand directed to a desired receptor within the body. The resulting anti-idiotypic antibody binds to the same receptor as the ligand, due to the topological similarity of the anti-idiotypic antibody and the ligand. The anti-idiotypic antibodies employed in the present invention are made according to well established hybridoma technology of Kohler and Milstein as is known to one of skill in the art and as modified by others (European Patent 0386275). As previously described, antibody fragments that retain the desired epitope for binding may be used. The whole or fragmented, natural or recombinant anti-idiotypic antibodies can be coupled to the photoactive molecule such as a chromophore, fluorophore, or photosensitizer by any one of the several methods known to one of ordinary skill in the art.

The inventive diagnostic compositions comprise anti-receptor internal image antibody conjugates of formula 1, Ab-Dye wherein Ab is a whole or fragmented internal image antibody which retain binding affinities directed at a particular biological receptor. The internal image antibodies of the invention are directed at receptors for steroids, cardiac glycosides (e.g., digoxin), somatostatin, bombesin, neurotensin, cholecystokinen (CCK) and heat stable toxin, (see, for example, U.S. Pat. No. 5,518,888, which is expressly incorporated by reference herein in its entirety). In some embodiments, a linker (L) links Ab and Dye, represented as Ab-L-Dye. The linker may be —HNCONH—, —HNCSNH—, —HNCO—, —CONH—, —S(CH$_2$)$_m$CONH—, and —S—(N-succinimido)-(CH$_2$)$_n$CONH—, where m and n vary from 1 to 10. The dye is a fluorophore or a chromophore capable of absorbing or emitting light having a wavelength in the range of 300-1200 nm.

As used herein, the terms "ST" and "native ST" are used interchangeably and are meant to refer to heat-stable toxin (ST) which is a peptide produced by *E. coli*, as well as other organisms. STs are naturally occurring peptides which 1) are naturally produced by organisms, 2) which bind to the ST receptor and 3) which activate the signal cascade that mediates ST-induced diarrhea.

As used herein, the term "ST receptor" is meant to refer to the receptors found on colorectal cells, including local and metastasized colorectal cancer cells, which bind to ST. In normal individuals, ST receptors are found exclusively in cells of intestine, in particular in cells in the duodenum, small intestine (jejunum and ileum), the large intestine, colon (cecum, ascending colon, transverse colon, descending colon and sigmoid colon) and rectum.

In one particular embodiment of a diagnostic conjugate, Ab is directed at a receptor for steroids, cardiac glycosides, bombesin, neurotensin, or ST; L is a linker and may be —HNCONH—, —HNCSNH—, —HNCO—, or —S—(N-succinimido)-(CH$_2$)$_n$CONH— and n varies from 1 to 6; and the dye is a chromophore or fluorophore derived from a cyanine, an indocyanine, a phthalocyanine, a rhodamine, a phenoxazine, a phenothiazine, a phenoselenazine, a fluorescein, a porphyrin, a benzoporphyrin, a squaraine, a corrin, a croconium, an azo compound, a methine dye, an indolenium dye, and the like.

In another particular embodiment of a diagnostic conjugate, Ab is directed at a receptor for steroids, bombesin, neurotensin, or heat stable toxin; L is a linker and may be —HNCONH—, —HNCO—, or —S—(N-succinimido)-$(CH_2)_n$CONH— and n varies from 1 to 6; and the dye is an aromatic or a heteroaromatic radical derived from a cyanine, an indocyanine, a rhodamine, a phenothiazine, a fluorescein, or an azo compound.

The inventive therapeutic compositions comprise anti-receptor internal image antibody conjugates of formula 2, Ab-PS-Q wherein Ab is a whole or fragmented internal image antibody directed at a particular biological receptor. The internal image antibodies of the invention are directed at receptors for steroids, cardiac glycosides (e.g., digoxin), somatostatin, bombesin, cholecystokinen, neurotensin, or heat stable toxin. A linker L may link Ab and PS or PS-Q, represented as Ab-L-PS(-Q), and L may be —HNCONH—, —HNCSNH—, —HNCO—, —CONH—, —S$(CH_2)_m$CONH—, or —S—(N-succinimido)-$(CH_2)_n$CONH—, where m and n vary from 1 to 10. PS is a photosensitizing aromatic or a heteroaromatic radical derived from a benzene, a polyfluorobenzene, a naphthalene, a naphthoquinone, an anthracene, an anthraquinone, a phenanthrene, a tetracene, a naphthacenedione, a pyridine, a quinoline, an isoquinoline, an indole, an isoindole, a pyrrole, an imidiazole, a pyrazole, a pyrazine, a purine, a benzimidazole, a benzofuran, a dibenzofuran, a cabrioles, an acridine, an acridone, a phenanthridine, a thiophene, a benzothiophene, a dibenzothiophene, a xanthene, a xanthone, a flavone, a coumarin, or an anthacyline. Q is either a precursor for producing reactive intermediates such as free radicals, nitrenes, carbenes, and the like, and may be an azide (—$N_3$), a cyclic azo compound (—N=N—), or a sulfenate (—O—S—).

In one particular embodiment of a therapeutic conjugate, the conjugates have the general formula Ab-L-PS-Q wherein Ab is directed at a receptor for steroids, bombesin, neurotensin, or heat stable toxin; L is a linker of —HNCONH—, —HNCSNH—, —HNCO—, or —S—(N-succinimido)-$(CH_2)_n$CONH— and n varies from 1-6; PS is a benzene, a polyfluorobenzene, an anthracene, an anthraquinone, a naphthacenedione, a quinoline, an isoquinoline, an indole, an acridine, an acridone, a phenanthridine, a xanthene, a xanthone, or an anthacyline; and Q is an azide (—$N_3$) or a sulfenate (—O—S—).

In another particular embodiment of a therapeutic conjugate, the conjugates have the general formula Ab-L-PS-Q wherein Ab is directed at a receptor for steroids, bombesin, neurotensin, or heat stable toxin; L is a linker of —HNCONH—, —HNCO—, or —S—(N-succinimido)-$(CH_2)_n$CONH— and n varies from 1 to 6; PS is a tetrafluorobenzene, a phenanthridine, a xanthone, an anthraquinone, an acridine, or an acridone; and Q is an azide (—$N_3$).

Figure 1:
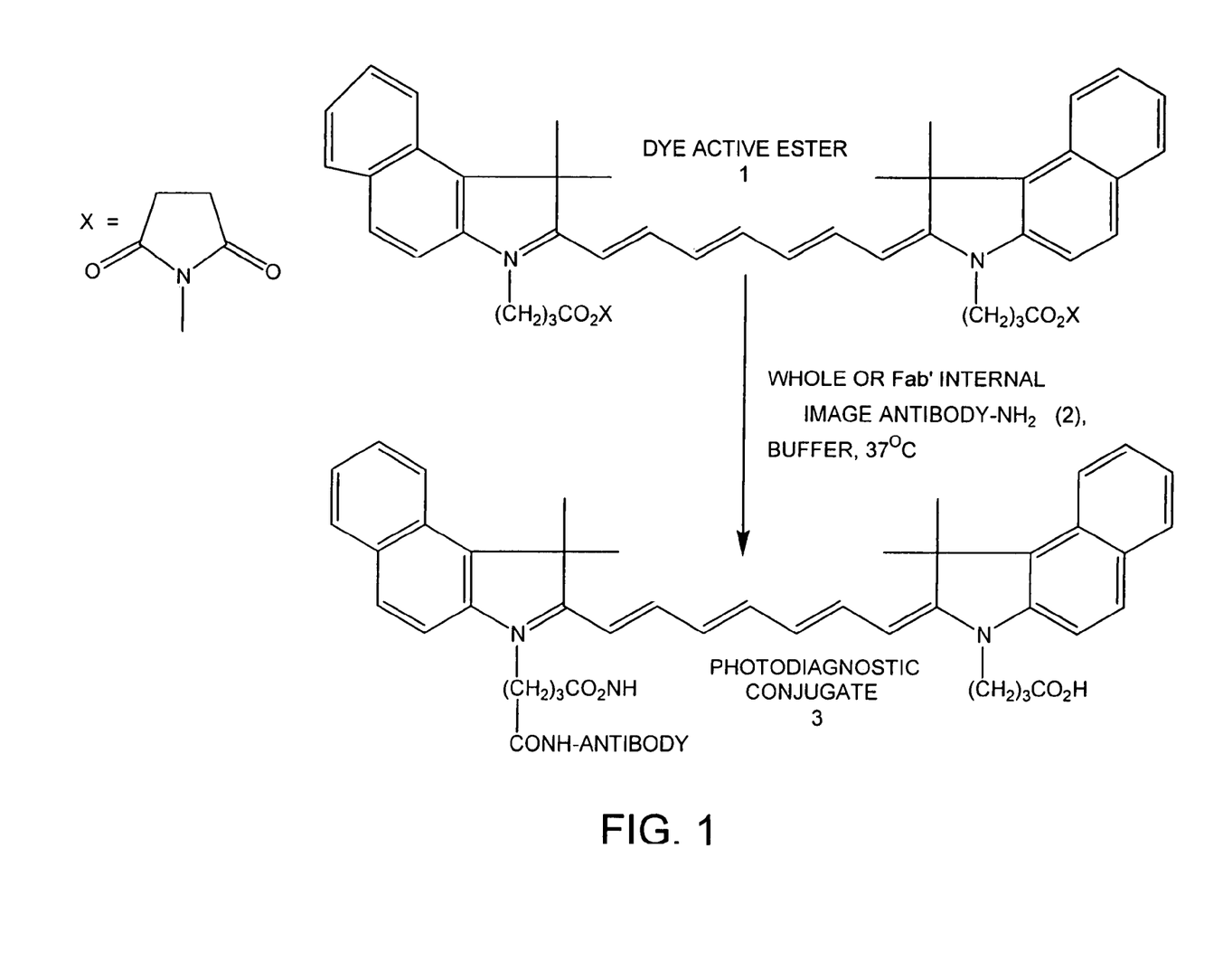
FIG. 1 is a schematic pathway for the synthesis of a photodiagnostic conjugate.
Figure 2:
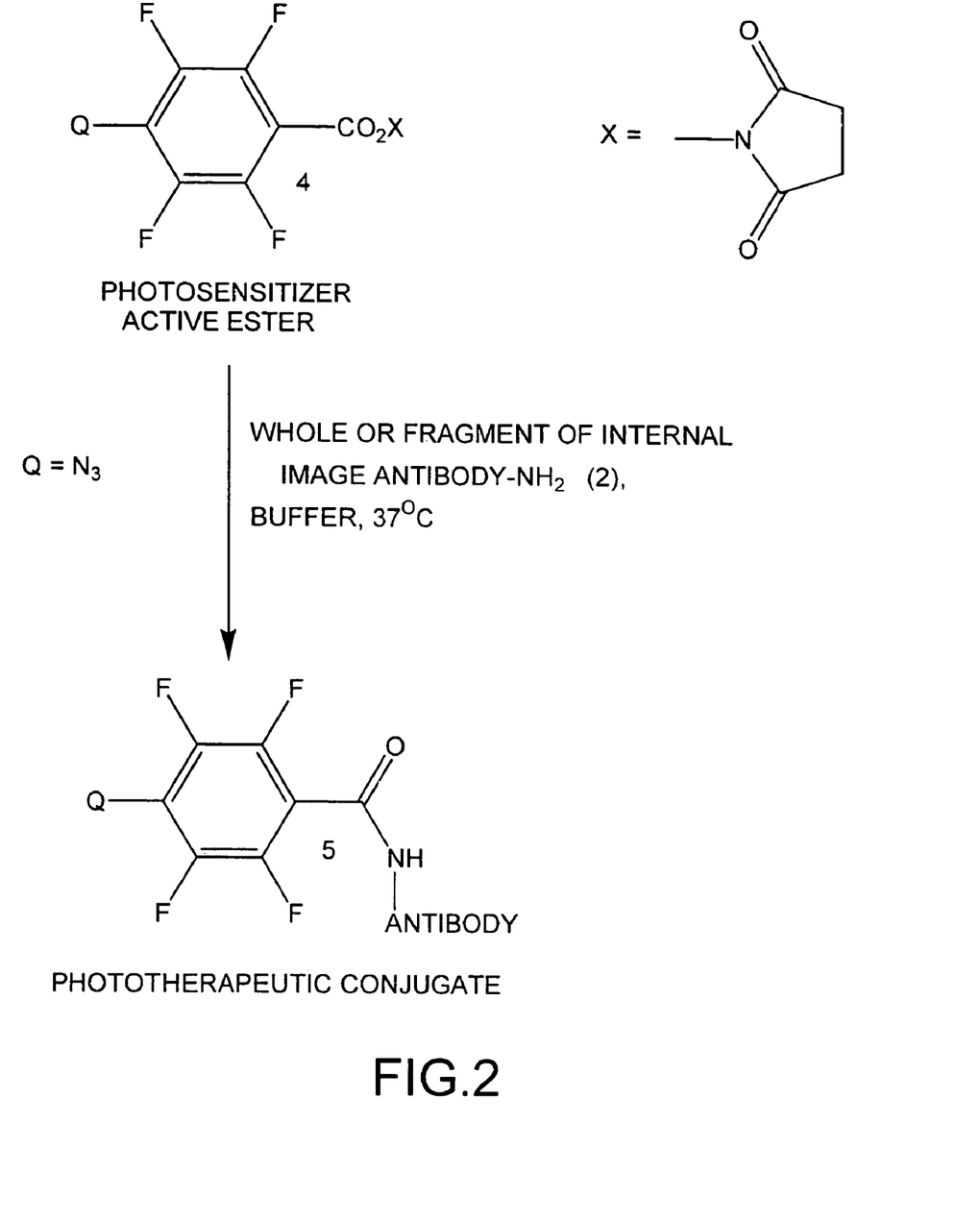
FIG. 2 is a schematic pathway for the synthesis of a phototherapeutic conjugate.

The internal image antibodies can be labeled or coupled with dyes or photosensitizers (i.e., effector molecules) in either a non-selective or selective manner. In non-selective labeling, the photoactive molecule is bound at any location on the anti-idiotypic antibody. This may be accomplished, for example, by using the active esters of the chromophore, fluorophore, or photosensitizer. In selective labeling or coupling, the photoactive molecule is attached distally from the receptor-binding site of the antibody. This may be accomplished, for example, by using a bifunctional maleimido reagent that reacts with a free sulfhydryl group generally found in the fragmented antibodies. Both selective and non-selective labeling are known to one skilled in the art and have been described by Nicolotti et al. (U.S. Pat. No. 4,732,974) and by Achilefu et al. (*Investigative Radiology*, 2000, 35(8), 479-485), each of which is incorporated by reference herein in its entirety. A typical preparation of a whole or Fab' internal image antibody conjugate bearing a chromophore or a fluorophore is shown in FIG. 1, and that for a photosensitizer is shown in FIG. 2. Both types of preparations are described in detail in the Examples.

Methods of performing diagnostic and/or therapeutic procedures with compositions of the invention are also disclosed. The methods encompass administering to a patient an effective amount of the compositions of the invention contained in a pharmaceutically acceptable formulation.

The compositions are administered in doses or concentrations that are effective to achieve the desired diagnostic or therapeutic objective. Such doses or concentrations may vary widely, depending upon the particular complex employed, the organs or tissues to be examined, the equipment employed in the clinical procedure, and the like. In one embodiment, the dose of the photoactive conjugate may vary from about 0.1 mg/kg body weight to about 500 mg/kg body weight. More typically, the dose is in the range of about 0.5 mg/kg body weight to about 2 mg/kg body weight. In another embodiment, a dose for parenteral administration contains the photoactive conjugate in a concentration ranging from about 1 μM to about 0.5 M. Preferred parenteral formulations have a concentration in the range of about of 1 mM to about 10 mM. The methods for administering different doses and compositions of the conjugates for photodiagnostic and phototherapeutic purposes are known to one skilled in the art.

The inventive compositions can be prepared in diagnostic or therapeutic formulations for enteral (oral or rectal), parenteral, topical or cutaneous administration. Topical or cutaneous delivery may also include aerosol formulations. The compositions may also contain conventional pharmaceutical carriers and excipients appropriate for the type of administration contemplated. Other agents which may be included are stabilizing agents and skin penetration enhancing agents. Such solutions also may contain pharmaceutically acceptable buffers, emulsifiers, surfactants, and electrolytes such as sodium chloride. Acceptable carriers include those that are suitable for injection such as aqueous buffer solutions, e.g., tris(hydroxymethyl)aminomethane and its salts, phosphate, citrate, bicarbonate, and the like, sterile water for injection, physiological saline, and balanced ionic solutions containing chloride and/or bicarbonate salts of normal blood plasma cations such as $Ca^{2+}$, $Na^+$, $K^+$ and $Mg^{2+}$. The carriers may contain a chelating agent, e.g., ethylenediaminetetraacetic acid, calcium disodium salt, or other pharmaceutically acceptable chelating agents.

Formulations for enteral administration may vary widely, as is well known in the art. In general, such formulations are liquids, which include an effective amount of the complexes in aqueous solution or suspension. Such enteral composition may optionally include buffers, surfactants, emulsifiers, thixotropic agents, and the like. Compositions for oral administration may also contain flavoring agents and other ingredients for enhancing their organoleptic qualities. Formulations for topical delivery may also contain liquid or semisolid excipients to assist in the penetration or aerosol spray of the photoactive molecule.

After administration, the photoactive conjugate is allowed to accumulate in the region of interest. For photoactivation, the region is illuminated with light having a wavelength in the range of about 300 nm to about 1200 nm, preferably in the range of about 350 nm to about 850 nm. In phototherapeutic procedures the target site is exposed to light sufficient to activate the photosensitizer and/or precursor to induce necrosis or apotosis of the impaired tissue. Light of low energy is usually needed to activate the photosensitizer and light of high energy is needed to activate the precursor. If the region of interest is, for example a lesion on the skin surface, the region can be directly illuminated. Otherwise, endoscopic catheters equipped with a light source may be employed to provide the photodiagnostic and/or the phototherapeutic effect. The intensity, power, and duration of the illumination, and the wavelength of the light may vary widely depending on the body location, the lesions site, the effect to be achieved, etc. The fluence rate is preferably, but not always, kept below 200 mW/cm$^2$ to minimize thermal effects. Appropriate power depends on the size, depth, and the pathology of the lesion, as is known to one skilled in the art. Detection of the chromophore or fluorophore in the localized tissues may be by absorbance, fluorescence, scattering, planar imaging, or tomographic imaging methods known in the art.

The internal image anti-idiotypic antibodies and the corresponding photoactive conjugates can be prepared in accordance with a typical procedure pertaining to digoxin receptor set forth in Example 1, which is not intended to be limiting. Digoxin, like steroids, belongs to a general class of perhydrocyclopentanophenanthrene molecules and binds to the digoxin receptor, which is a special type of myocardial sodium-potassium ATPase. It is believed that the labeled digoxin internal image antibodies may be useful in the diagnosis of some coronary disorders and/or may supplement the information gained from the use of myocardial perfusion agents.

EXAMPLE 1

Preparation of Digoxin Internal Image Antibody Fab' Fragments and Conjugation to an Optical Diagnostic Agent.

(a) Fusion of Mouse Myeloma Cells with the Spleen Cells of AJ Mice Immunized with Balb-C Mouse Anti-Digoxin Antibody.

Monoclonal antibodies were produced using standard hybridoma technology, as is known to one of ordinary skill in the art. Briefly, two AJ mice were immunized with murine (Balb-C) monoclonal anti-digoxin antibody (Medex Laboratories). A booster injection was given three weeks after the primary immunization and the spleens were removed after three days. Mouse myeloma and spleen cells were washed three times with Dulbecco's Modified Eagle Medium (DME) and suspended in DME (10 ml). A 5 mL portion of each of these cell suspensions was mixed and centrifuged. The supernatant was discarded and the pellet was treated with 1 mL polyethylene glycol (added over a 45 second period), 3 mL DME (added over a 30 second period), and an additional 9 mL of DME was added over a 30 second period. The cells were allowed to stand at ambient temperature for eight minutes, and at 37° C. for two minutes. The cells were centrifuged, suspended in medium that contains hypoxanthine, aminopterin, and thymidine (HAT medium) (10 mL), and distributed in microtiter plates. The cells were allowed to grow and were screened by a radioimmunoassay procedure approximately 3 weeks after fusion.

(b) Screening of Anti-Idiotypic Antibodies for Digoxin.

A 75 μL portion of affinity purified goat anti-mouse antibody (2 mg/mL) was diluted with phosphate buffered saline (PBS) (150 mL) and 200 μL aliquots were placed into each well of a microtiter plate. The plates were incubated at 37° C. for four hours. The wells were washed with water (three times), treated with 3% BSA solution (200 μL), and then incubated for one hour. The wells were washed again with water (three times), treated with the supernatants from the cell culture (150 μL), and then allowed to incubate at ambient temperature for about 18 hours. The wells were washed with water (three times), treated with $^{125}$I labeled goat anti-digoxin (100 μL) and incubated for four hours. The plates were subsequently washed and the wells were counted for $^{125}$I. A total of 39 positive wells were identified.

The supernatants (100 μL) from the corresponding positive wells were mixed with $^{125}$I-digoxin (50 μL) and were placed for one hour in the microtiter plates which were previously coated with about 0.5 μg of monoclonal mouse anti-digoxin antibody. The plates were washed with water three times and the amount of radioactivity was measured. Inhibition of $^{125}$I-digoxin binding, compared to the control, indicated a positive test for anti-idiotypes. Four positive wells were identified.

(c) Preparation of Fab' Fragments of Anti-Idiotypic Digoxin Antibody.

Ascites fluid is obtained in the usual manner by injecting hybridoma cells, prepared according to the procedure outlined in the above section (a), into mouse peritoneum. The anti-idiotypic digoxin antibody is purified from the fluid by three successive precipitations with saturated ammonium sulfate in 20 mM phosphate buffer, pH 6.8. Thereafter, the precipitated protein is dialyzed exhaustively against 20 mM phosphate buffer, pH 6.8. The solubilized monoclonal antibody is purified by ion-exchange chromatography (Whatman C-52 column, 0 to 500 mM NaCl gradient in sodium phosphate buffer, pH 6.8). The desired fraction containing the anti-idiotypic digoxin antibody is collected and stored in the same buffer at 4° C.

The Fab' fragment is obtained using a modification of the method reported in Parham et al., *J. Immunol. Methods,* 1982, 53, 133-173. The desired amount of the anti-idiotypic digoxin antibody (absorbance of 1% solution at 280 nm=14.4) and cysteine-free papain (Worthington, 2 times crystallized) in the ratio of 1:20 is incubated at 37° C. using ten times the volume of digestion buffer (100 mM sodium acetate, 3 mM disodium EDTA, pH 5.5) until the reaction is completed (3-16 hours), as determined by sodium dodecyl sulfate polyacrylamide gel electrophoresis (SDS-PAGE). The digestion mixture is diafiltered (Amicon flow cell, PM-10 membrane) at 4° C. using 5 mM Tris-HCl buffer, pH 7.2. The anionic Fc fragment is removed from the mixture by ion exchange chromatography (Whatman 52 column, 0 to 100 mM NaCl gradient in 5 mM Tris-HCl buffer, pH 7.2). The F(ab')$_2$ fragment and inactivated papain are contained in the void volume. The F(ab')$_2$ fragment is further purified from the papain by Sephadex G-100 size exclusion chromatography using 5 mM Tris-HCl buffer, pH 7.2 as the eluant. The desired antibody fragment elutes in the void volume and is characterized by SDS-PAGE. The F(ab')$_2$ fragments are stored in aliquots at −70° C.

The F(ab')$_2$ dimer obtained by papain digestion of the whole antibody is further cleaved to the desired Fab' using thiol reagents such as cysteine or β$_2$-mercaptoethanol. The F(ab')$_2$ is incubated at room temperature in the presence of either 10 mM cysteine or β$_2$-mercaptoethanol until the reaction is complete as determined by SDS-PAGE (one to four hours). The reaction is stopped with the addition of 30 mM iodoacetamide. Excess reducing agent, iodoacetamide, and other low molecular weight fragments is removed by size exclusion Sephadex G-25 chromatography using phosphate buffered saline, pH 7.4, (PBS), as the eluant. The Fab' fragment thus obtained is used as soon as possible in order to prevent oxidation of the sulfhydryl groups.

(d) Conjugation of Fab' Fragments with an Optical Diagnostic Agent.

The conjugation procedure is carried out in a manner similar to that for anti-CEA antibody, as reported in Achilefu et al., *Investigative Radiology*, 2000, 35, 479-485, which is expressly incorporated herein by reference in its entirety.

With reference to FIG. 1, a mixture of the Fab' fragment (2) and about 20 fold molar excess of the dye active ester (1) is incubated in PBS for four hours. The photodiagnostic conjugate (3) is then purified by Sephadex G-25 size exclusion chromatography using PBS as the eluent, and is subsequently lyophilized.

EXAMPLE 2

Preparation of Digoxin Internal Image Antibody Fab' Fragments and Conjugation to a Phototherapeutic Agent.

The Fab' fragments (2) obtained in Example 1, step (c) are used for conjugation to a phototherapeutic agent. The conjugation procedure is carried out in a manner similar to the one published previously for human serum albumin (Achilefu et al., *Investigative Radiology*, 2000, 35, 479-485), which is expressly incorporated by reference in its entirety.

With reference to FIG. 2, a mixture of the Fab' fragment (2) and about 20 fold molar excess of the photosensitizer active ester (4), is incubated in PBS for four hours. The phototherapeutic conjugate (5) is purified by Sephadex G-25 size exclusion chromatography using PBS as the eluant, and is subsequently lyophilized.

EXAMPLE 3

Preparation of Whole Digoxin Internal Image Antibodies and Conjugation to an Optical Diagnostic Agent.

Whole digoxin internal image antibodies obtained in Example 1, steps (a) and (b) were used for conjugation to a photodiagnostic agent. The conjugation procedure was carried out in a manner similar to the one published previously for human serum albumin (Pandurangi et al., *Journal of Organic Chemistry*, 1998, 63, 9019-9030).

EXAMPLE 4

Whole digoxin internal image antibodies obtained in Example 1, steps (a) and (b) were used for conjugation to a phototherapeutic agent. The conjugation procedure was carried out in a manner similar to the one published previously for human serum albumin (Pandurangi et al., *Journal of Organic Chemistry*, 1998, 63, 9019-9030).

It should be understood that the embodiments of the present invention shown and described in the specification are only specific embodiments of the inventors who are skilled in the art and are not limiting in any way. Therefore, various changes, modifications or alterations to those embodiments may be made or resorted to without departing from the spirit of the invention and the scope of the following claims. In addition, each of the references previously disclosed is expressly incorporated by reference herein in its entirety.

What is claimed is:

1. A method of diagnosing a patient, the method comprising:
   (a) selecting a ligand that binds to a heat stable toxin biological receptor;
   (b) preparing a first generation of monoclonal antibodies against the receptor binding ligand;
   (c) isolating the first generation of monoclonal antibodies;
   (d) preparing monoclonal anti-idiotypic antibodies against the first generation of monoclonal antibodies to result in internal image anti-receptor antibodies;
   (e) isolating the internal image anti-receptor antibodies;
   (f) conjugating the internal image anti-receptor antibodies to a photoactive dye;
   (g) administering a concentration of the conjugate of step f to a patient effective to diagnose the patient;
   (h) allowing the conjugate to accumulate at a target site within the patient; and
   (j) exposing the target site to light sufficient to activate the photoactive dye to image the target site.

2. The method of claim 1 wherein said receptor-binding ligand is selected from the group consisting of peptides, and peptidomimetics.

3. The method of claim 1 wherein said dye is selected from the group consisting of cyanines, indocyanines, phthalocyanines, rhodamines, phenoxazines, phenothiazines, phenoselenazines, fluoresceins, porphyrins, benzoporphyrins, squaraines, corrins, croconiums, azo compounds, methine dyes, and indolenium.

4. The method of claim 1 wherein said effective concentration of the internal image antibody conjugate ranges from about 0.1 mg/kg body weight to about 500 mg/kg body weight.

5. The method of claim 1 wherein the effective concentration of the internal image antibody conjugate ranges from about 0.5 mg/kg body weight to about 2 mg/kg body weight.

6. The method of claim 1 wherein imaging is selected from at least one of absorbance, fluorescence, scattering, and combinations thereof.

7. The method of claim 1 wherein binding of the ligand to a heat stable toxin receptor is used in diagnosis of colorectal cancer.

8. A method of imaging a body region of a patient, the method comprising
   administering to a patient a photodiagnostic composition comprising at least one pharmaceutical carrier or excipient and an internal image antibody to a heat stable toxin biological receptor conjugated to a photoactive dye at a dose effective for photodiagnosis, wherein the dye is selected from the group consisting of cyanines, indocyanines, phthalocyanines, rhodamines, phenoxazines, phenothiazines, phenoselenazines, fluoresceins, porphyrins, benzoporphyrins, squaraines, corrins, croconiums, azo compounds, methine dyes, and indolenium, and;
   thereafter providing light sufficient to activate said photoactive dye in said body region to image said body region.

9. The method of claim 8 wherein light is provided at a wavelength in the range of about 300 to 1200 nm.

10. The method of claim 8 wherein imaging is by a method selected from the group consisting of absorbance, fluorescence, scattering, and combinations thereof.

11. The method of claim 8 wherein said effective dose is in the range of about 0.1 mg/kg to about 500 mg/kg body weight.

12. The method of claim 8 wherein binding of Ab to a heat stable toxin receptor is used in diagnosis of colorectal cancer.

* * * * *

UNITED STATES PATENT AND TRADEMARK OFFICE
CERTIFICATE OF CORRECTION

PATENT NO. : 7,431,925 B2  Page 1 of 1
APPLICATION NO. : 10/761634
DATED : October 7, 2008
INVENTOR(S) : Raghavan Rajagopalan et al.

It is certified that error appears in the above-identified patent and that said Letters Patent is hereby corrected as shown below:

Title page
(75) Inventors

Inventors Bugaj, Achilefu, and Dorshow change State of residence from "MI" to -- MO --.

Signed and Sealed this

Twenty-seventh Day of January, 2009

JOHN DOLL
*Acting Director of the United States Patent and Trademark Office*